United States Patent
Spencer

(10) Patent No.: US 6,193,702 B1
(45) Date of Patent: Feb. 27, 2001

(54) COMBINATION REUSABLE UNDERGARMENT AND DISPOSABLE ABSORBENT ARTICLE

(76) Inventor: Gorham Gennette Spencer, 88 Depeyster St., Sleepy Hollow, NY (US) 10591

( * ) Notice: Subject to any disclaimer, the term of this patent is extended or adjusted under 35 U.S.C. 154(b) by 0 days.

(21) Appl. No.: 09/247,781

(22) Filed: Feb. 9, 1999

(51) Int. Cl.[7] ........................................ A61F 13/15
(52) U.S. Cl. .......................... 604/385.03; 604/385.14; 604/385.13; 604/387
(58) Field of Search .................. 604/393, 394, 604/395–402; 24/587, 576

(56) References Cited

U.S. PATENT DOCUMENTS

| | | | |
|---|---|---|---|
| Re. 26,939 | * 8/1970 | Hervey et al. | 604/399 |
| 2,016,355 | * 10/1935 | Alsop . | |
| 3,117,577 | * 1/1964 | Mosier | 604/399 |
| 3,162,196 | * 12/1964 | Salk | 604/399 |
| 3,312,981 | * 4/1967 | McGuire et al. . | |
| 3,395,705 | * 8/1968 | Hervey et al. | 604/399 |
| 4,338,939 | * 7/1982 | Daville | 604/399 |
| 4,677,697 | 7/1987 | Hayes . | |
| 4,834,738 | 5/1989 | Kielpikowski et al. . | |
| 5,217,447 | * 6/1993 | Gagnon | 604/397 |
| 5,241,710 | * 9/1993 | Lockhart | 604/396 |
| 5,243,974 | * 9/1993 | Allen | 604/400 |
| 5,300,058 | 4/1994 | Goulait et al. . | |
| 5,342,340 | 8/1994 | Kichefski et al. . | |
| 5,464,401 | 11/1995 | Hasse et al. . | |
| 5,507,735 | * 4/1996 | Van Iten et al. | 604/385.1 |
| 5,891,122 | * 4/1999 | Coates | 604/385.1 |

* cited by examiner

*Primary Examiner*—Sharon Kennedy
*Assistant Examiner*—Michael M Thompson

(57) ABSTRACT

A reusable undergarment (10) in the shape of a panty of lightweight stretchable fabric having a seat (16) of fluid resistant material where one or more female receiving grooves (20) are stitched or depressed in at a standard spacing running transverse to the longitudinal axis of the reusable undergarment seat (16). A disposable absorbent article (22) of pre determined material where on the bottom (28) is stitched or depressed one or more male insert ridges (30) at a standard spacing corresponding to that of the female receiving grooves (20) in the seat of the reusable undergarment.

8 Claims, 2 Drawing Sheets

COMBINATION REUSABLE UNDERGARMENT AND DISPOSABLE ABSORBENT ARTICLE

BACKGROUND

1. Field of Invention

Figure 1:
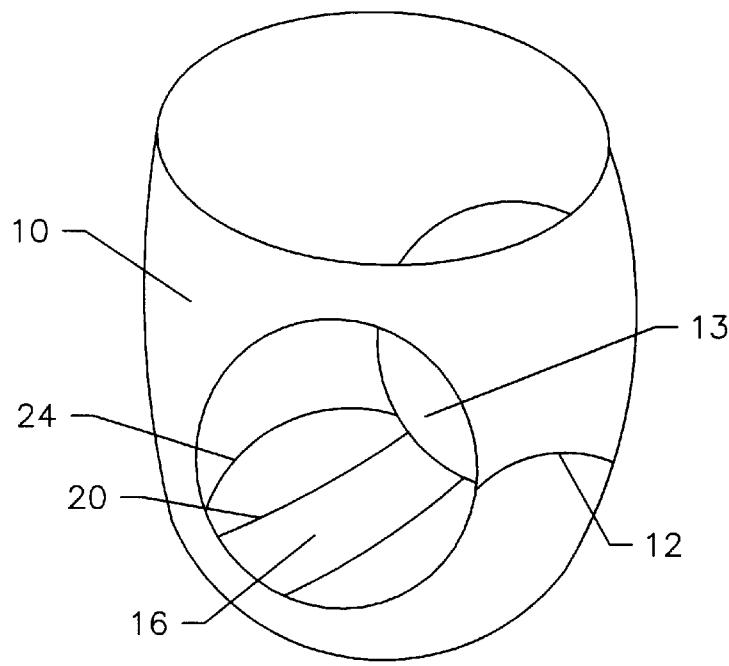

This invention relates to a combination reusable undergarment and disposable absorbent article having a mechanical fastening system, such garments would include those worn by adults or children.

2. Description of Prior Art

Women, infants and incontinent individuals wear protective garments to receive, absorb and retain bodily exudate and excrement such as mensus, urine and feces. The use and variety of these protective garments are well known, particularly sanitary napkins, panty liners, disposable training pants, and incontinent pads; and are available in the marketplace.

Currently available disposable absorbent articles particularly sanitary napkins and panty liners are positioned in the seat of the undergarment, such as women's panties and secured by pressure sensitive adhesive. While the use of adhesive is common, there are disadvantages such as comfort, residual build-up on panty, and adhesive contamination.

A common problem with the disposable absorbent article such as the sanitary napkin is that it frequently shifts out of its original position during wear caused by body movement such as walking, bending, turning over, running or exercising. If the disposable absorbent article uses an adhesive to secure it to the seat of the panty, then this shifting of the disposable absorbent article can result in the adhesive sticking to itself causing "bunching" of the disposable absorbent article. Another common problem with the disposable absorbent article having pressure sensitive adhesive is that it frequently comes loose from the panty seat when the panty is being pulled down particularly if the wearer's panties or pants are tight fitting. This can result in the adhesive sticking to itself, to the body of the wearer or to an extraneous surface.

An alternative to pressure sensitive adhesive are mechanical fasteners. Disposable absorbent articles using mechanical fasteners generally do not suffer from "bunching" as do disposable absorbent articles using pressure secured adhesive. Still, disposable absorbent articles using mechanical fasteners will suffer from misalignment in the seat of the wearer's panty as a result of shifting of the central absorbent means. In the Nether Garment M. H. McGuire ETAL U.S. Pat. No. 3,312,981 the devices used to hold the sanitary napkin in position are elastic straps sewn at their ends to the crotch fabric to form loops into which the ends of a sanitary napkin may be extended and while the pad is secured at the front end and back end of the panty there is no continuity of security which therefore could lead to misalignment of the sanitary napkin during normal daily activities such as bending, walking etc. The Nether Garment B. S. ALSOP U.S. Pat. No. 2,016,355 uses pockets at the front and rear of the panty seat to secure the sanitary napkin therefore lacking in continuity of security.

Therefore there is a need for a reusable receiving undergarment comprising a mechanical receptor that holds a disposable absorbent article comprising a mechanical insert in place without unwanted shifting of the central absorbent means. There is also a need for a disposable absorbent article comprising a mechanical insert which can attach the disposable absorbent article securely to the receiving undergarment.

It is therefore the object of the present invention to provide a reusable receiving under garment comprising a mechanical receptor that holds a disposable absorbent article comprising a mechanical insert securely in the seat of the garment without popping loose upon pulling up or pulling down of garment.

Another object of the present invention is to provide a reusable receiving undergarment comprising mechanical receptor that holds a disposable absorbent article comprising mechanical insert, securely in the seat of the undergarment without unwanted shifting of the disposable absorbent article.

Another object of the present invention is to provide a reusable receiving under garment comprising a mechanical receptor that holds a disposable absorbent article comprising a mechanical insert, securely in the seat of the under garment that will keep the disposable absorbent article in intimate contact with the body of the wearer.

Another object of the present invention is to provide an additional reservoir for bodily exudates or excrement such as menus or urine.

DRAWING FIGURES

Figure 2:
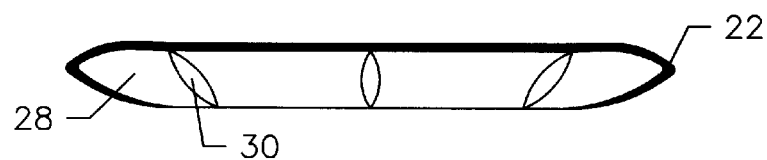
Figure 3:
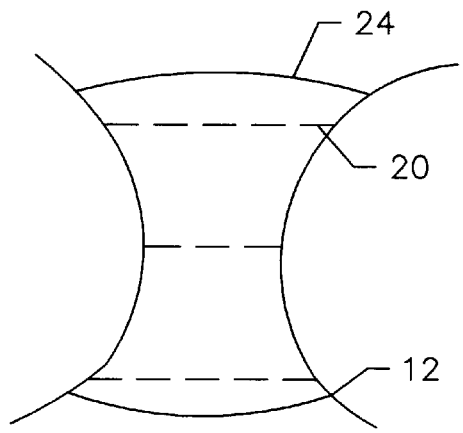
Figure 4:
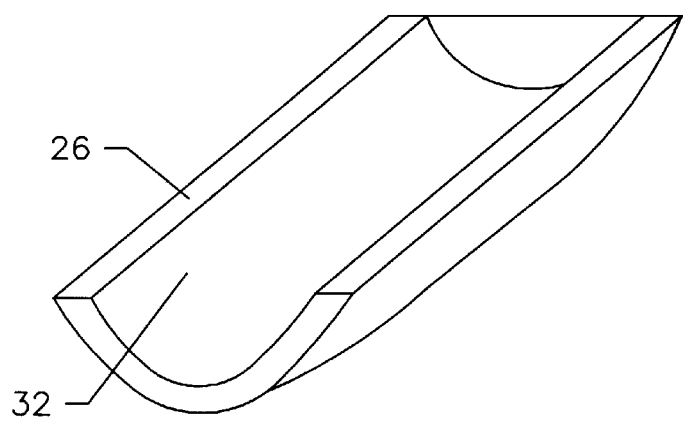
Figure 5:
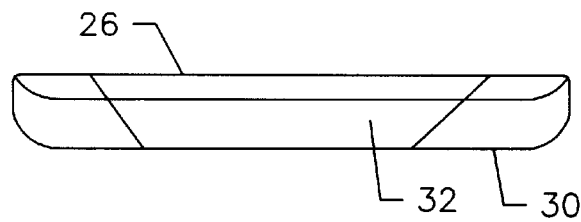
Figure 6:
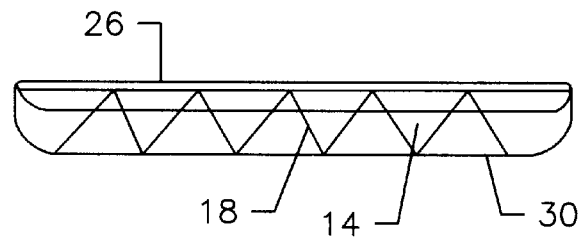
Figure 7:
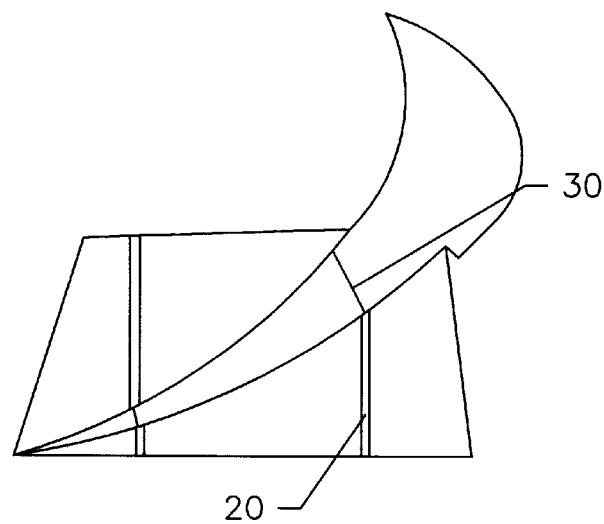

FIG. 1 shows a partial side view of a reusable under garment with female receiving grooves at a standard spacing from each other and running transverse to the longitudinal axis of the seat of the undergarment FIG. 2 shows a bottom view of a disposable absorbent article with male insert ridges at a standard spacing from each other, to correspond to receiving grooves in the reusable under garment seat FIG. 3 shows a top view of a reusable under garment seat with female receiving groove FIG. 4 shows a side view of a male insert ridge FIG. 5 shows a cross sectional view of a male insert ridge with continuous single reservoir FIG. 6 shows a cross sectional view of a male insert ridge with minute individual reservoirs FIG. 7 shows partial side view overlay of a disposable absorbent article and seat of a reusable under garment

REFERENCE NUMERAL IN DRAWINGS

| | |
|---|---|
| 10 reusable under garment | 30 male insert ridge |
| 12 front panty seat seam | 32 continuous single reservoir |
| 13 hole for leg | 14 minute individual reservoir |
| 16 reusable under garment seat | 18 wall of minute reservoir |
| 20 female receiving groove | 22 disposable absorbent article |
| 24 rear seat seam | 26 absorbent material |
| 28 bottom of disposable absorbent article | |

SUMMARY

In accordance with the present invention a combination reusable under garment with the seat of the under garment having female receiving grooves, and a disposable absorbent article where the underside of the article has male insert ridges.

DESCRIPTION—FIGS. 1 TO 7

A typical embodiment of the present invention is illustrated in FIG. 1 (Angled side view of reusable under garment) and FIG. 2 (bottom view of a disposable absorbent article). A reusable under garment 10 is the shape of a panty and comprises a light weight stretchable fabric which conforms to a range of body sizes for example-small-medium-large. A reusable under garment seat 16 comprises a fluid resistant fabric of minimum stretchability. A female receiving groove 20 is stitched or depressed into the reusable undergarment seat 16 running transverse to the longitudinal axis of the reusable undergarment seat 16. The preferred embodiment of the female receiving groove 20 is a flexible plastic. However the female receiving groove 20 can consist of any other material that is flexible and not easily fractured when bent.

A disposable absorbent article 22 comprises a material of predetermined texture for absorption on top 26 and a bottom 28 comprises a material impervious to fluids. A male insert ridge 30 is stitched to or depressed in the bottom layer of the disposable absorbent article 28 running transverse to the longitudinal axis of the disposable absorbent article 22 at a standard spacing corresponding to the female receiving grooves 20 in the reusable undergarment seat 16. A continuous single reservoir 32 is the topside of the male insert ridge 30. A wall of the minute individual reservoir 18 separates the individual reservoirs.

There are various possibilities with regard to the shape of the minute individual reservoir 14. An embodiment of a diamond shaped reservoir FIG. 6 is shown for illustration.

The interlocking of the male insert ridge 30 into the female receiving groove 20 is illustrated in FIG. 7.

OPERATION—FIG 7

The manner of attaching the disposable absorbent article 22 to the reusable undergarment 10 is identical to that presently used in the zipclosure locking seam bags, with the preferred embodiment utilizing transverse combinations of the groove and bead of the ziplock structure at each end and at the center of the pad/panty combination. The male insert ridge 30 is lined up to the corresponding female receiving groove 20 and starting at one end depress the male insert ridge 30 into the female receiving groove 20 by gently pressing from one side continually in sliding motion to the other side. To remove the disposable absorbent article 22 from the reusable undergarment 10 grasp the disposable absorbent article 22 at the point of entry of the male insert ridge 30 while firmly holding the seat of the reusable undergarment 16 at the corresponding point and gently pull the disposable absorbent article 22 off in a continuous motion transverse to the longitudinal axis of the panty seat.

RAMIFICATIONS AND SCOPE

The reader will see that the combination reusable undergarment and disposable absorbent article can be attached and removed as easily as closing and opening a zipclosure locker seam bag. The seat of the reusable undergarment is a second barrier against leakage of bodily fluids such as mensus or urine. The single continuous reservoir or plurality of minute reservoirs in the disposable absorbent article enhances containment of body fluids. The spacing of three transverse combination ridges and grooves as shown in the preferred embodiment serve to keep the disposable absorbent article smooth as well as facilitating quick and easy changes.

Although the description above contains many specifics, these should not be construed as limiting the scope of the invention, but as merely providing illustration of some of the presently preferred embodiments of this invention. For example an embodiment of minute diamond shaped reservoirs FIG. 6 is shown for illustration.

Thus the scope of the invention should be determined by the appended claims and their legal equivalents rather than by examples given.

I claim:

1. A combination reusable undergarment and disable absorbent article comprising:
   (a) a reusable undergarment—having a seat, wherein the undergarment is—of predetermined texture and size with one or more narrow, elongated female receiving grooves of predetermined size stitched or depressed into the seat of the undergarment at a standard spacing from each other and generally running transverse to a longitudinal axis of the seat of the undergarment
   (b) a disposable absorbent article of predetermined material and thickness having a topside and underside wherein the underside of the article one or more narrow elongated male insert ridges of predetermined size are stitched to or depressed in at a standard spacing corresponding to that of the female receiving grooves on the seat of the reusable undergarment whereby when the male ridges and female receiving grooves are pressed together there is interlocking of the underside of the disposable absorbent article to the seat of the reusable undergarment.

2. The disposable absorbent article in claim 1 wherein the elongated male insert ridges have a topside, the topside having a grooved surface providing a reservoir for bodily fluids or excrement such as mesus or urine.

3. The disposable absorbent article in claim 1 wherein the elongated male insert ridges have a topside, the topside having multiple grooves providing a plurality of minute individual reservoirs of predetermined shapes to receive bodily fluids or excrement such as mesus and urine.

4. The disposable absorbent article in claim 1 having at least one end on the topside of the article that is stitched or depressed a female receiving groove that will secure to a male insert ridge for disposal.

5. An undergarment and absorbent article comprising:
   (a) An undergarment;
   (b) An absorbent article;
   wherein one of said undergarment and absorbent article has at least one elongated male insert ridge thereon, and the other of said undergarment and absorbent article has at least one elongated female receiving groove thereon, such that when said female receiving groove and said male insert ridge are pressed together there is interlocking of said absorbent article and said undergarment.

6. The undergarment and absorbent article in claim 5 wherein the at least one elongated male insert ridge has a topside, the topside having a grooved surface providing a reservoir for bodily fluids or excrement such as mesus or urine.

7. The undergarment and absorbent article in claim 5 wherein the at least one elongated male insert ridges has a topside, the topside having multiple grooves providing a plurality of minute individual reservoirs of predetermined shapes to receive bodily fluids or excrement such as mesus and urine.

8. The undergarment and absorbent article in claim 5 having a topside and at least one end, wherein the topside of the article has a female receiving groove that will secure to a male insert ridge for disposal.

\* \* \* \* \*